United States Patent [19]

Gallian

[11] 4,140,756

[45] Feb. 20, 1979

[54] FILM-COATED MATRIX CORE TABLET

[75] Inventor: Claude E. Gallian, Evansville, Ind.

[73] Assignee: Mead Johnson & Company, Evansville, Ind.

[21] Appl. No.: 843,196

[22] Filed: Oct. 18, 1977

Related U.S. Application Data

[63] Continuation-in-part of Ser. No. 694,732, Jun. 10, 1976, abandoned.

[51] Int. Cl.$^2$ ............................................. A61K 9/24
[52] U.S. Cl. ...................................... 424/21; 424/19; 424/22; 424/153
[58] Field of Search .................................. 424/19–38, 424/153

[56] References Cited

U.S. PATENT DOCUMENTS

| | | | |
|---|---|---|---|
| 2,887,440 | 5/1959 | Greminger et al. | 424/35 |
| 3,062,720 | 11/1962 | Costello | 424/22 |
| 3,256,111 | 6/1966 | Singiser | 424/35 X |
| 3,317,394 | 5/1967 | Fryklof et al. | 424/22 |
| 3,325,365 | 6/1967 | Hotko et al. | 424/33 |
| 3,383,236 | 5/1968 | Brindamour | 424/35 X |
| 3,402,240 | 9/1968 | Cain et al. | 424/22 |
| 3,456,049 | 7/1969 | Hotko et al. | 424/22 |
| 3,538,214 | 11/1970 | Polli et al. | 424/19 |
| 3,917,813 | 11/1975 | Pedersen | 424/20 |

*Primary Examiner*—Shep K. Rose
*Attorney, Agent, or Firm*—R. E. Carnahan; R. H. Uloth

[57] ABSTRACT

A tablet for controlled release of a water soluble medicament or dietary supplement is comprised of a water insoluble wax-like matrix core containing the water soluble medicament and coated with a permeable erosion resistant polymeric film. The core constitutes 95% or more of the tablet weight.

19 Claims, 1 Drawing Figure

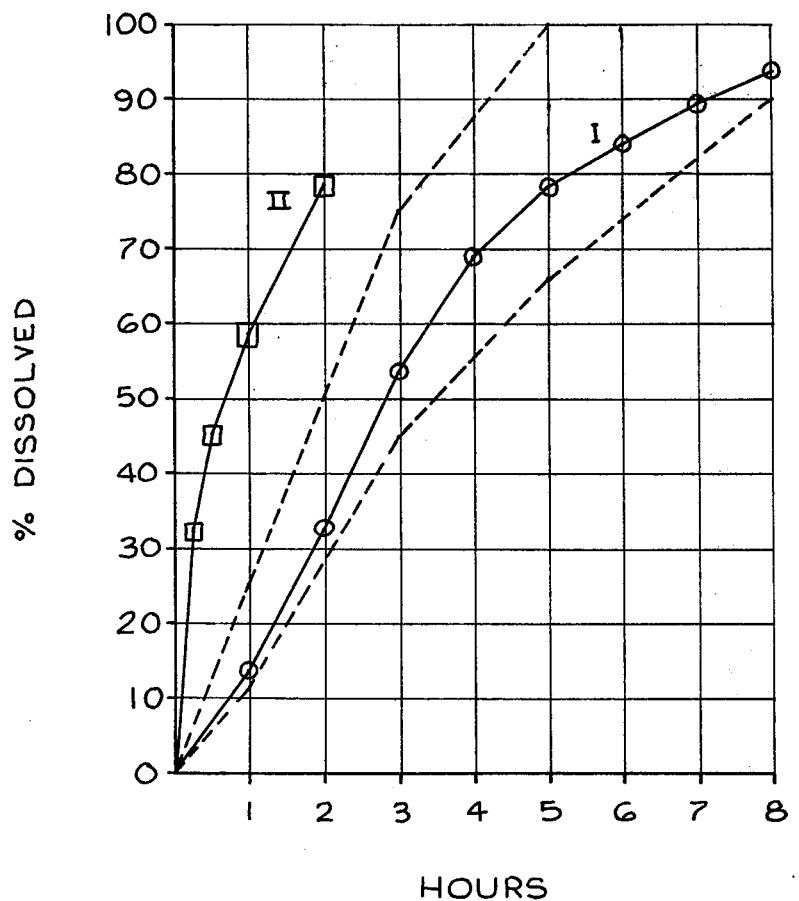

FILM-COATED MATRIX CORE TABLET

CROSS REFERENCE TO RELATED APPLICATION

This application is a continuation-in-part of application Ser. No. 694,732 filed June 10, 1976, now abandoned.

FIELD OF THE INVENTION

The present invention relates to drug bio-affecting and body treating compositions containing a water soluble active ingredient for controlled release over a prolonged dissolution period. The active ingredient may be an inorganic compound or an organic compound and is specifically adapted for the slow release of an alkali metal chloride and particularly potassium chloride over a period of several hours following ingestion.

DESCRIPTION OF THE PRIOR ART

Potassium depletion in man occurs in a number of clinical situations and most commonly in patients receiving diuretics. It is generally accepted that many patients on diuretics should receive a potassium supplement prophylactically. The normal daily requirement of potassium salts is about 40 meq. corresponding to 3 g. of potassium chloride. For therapeutic purposes, doses of 100 meq. per day of a potassium salt or more are sometimes required. The daily dosage of potassium chloride in this circumstance is thus about 7.5 g. Various pharmaceutical products have been made available for this purpose including liquid preparations as such or which are extemporaneously prepared by dissolving a tablet or powder in water prior to ingestion and enteric coated tablets containing various potassium salts. The use of enteric coated potassium salt containing tablets has been reported to occasionally produce intestinal ulcers, obstruction, hemorrhage, and even perforation. Liquid preparations require considerable amounts of water intake to avoid gastrointestinal disturbances and lack palatability for long term usage. Taste fatigue and the inconvenience frequently results in poor patient compliance.

The foregoing problems have been greatly reduced by controlled release oral potassium tablets which slowly release the potassium salt by gradual dissolution during transit through the gut. These tablets have the advantage of ease of administration over the liquid preparations and have greatly reduced ulcerogenic hazard compared to the enteric coated tablets which release the corrosive potassium salt contents all at once resulting in high local concentrations.

One difficulty associated with presently available controlled release potassium chloride tablets is that the daily dosage requirements involve swallowing an inconveniently large number of tablets. Presently available tablets contain either 500 mg. (Kaon-Cl Tabs TM, Warren-Teed Pharmaceuticals, Inc., Columbus, Ohio 43215) or 600 mg. (Slow-K ®, Ciba Pharmaceutical Company, Summit, N.J., 07901) of potassium chloride. Each of these products supplies potassium chloride in a sugar coated tablet in which the sugar coat constitutes a substantial portion of the tablet weight, and contributes little to the control of the release rate of the potassium chloride. Release over a prolonged period of time following ingestion is achieved by the gradual leaching of the water soluble medicament from a wax matrix. The daily dose of these products is from 5 or 6 tablets for prophylactic or maintenance therapy to 12 to 15 or more tablets for therapeutic purposes.

One object of the present invention is to provide a controlled release potassium chloride tablet for therapeutic and dietary supplement purposes containing substantially more potassium chloride than the foregoing tablets so that fewer tablets are required for the daily dose, thus fostering patient compliance with the dosage regimen.

The following references are representative of the prior art with respect to wax matrix controlled release tablets.

"Remington's Pharmaceutical Sciences", 14th Edition, Mack Publishing Company, 1970, page 1704. A controlled release tablet is described in which the drug tripellenamine hydrochloride is added to a molten mass of carnauba wax and stearyl alcohol. The mass is stirred until solidified and then reduced to granules by passing through a 16-mesh screen. After lubrication with magnesium stearate, the granules are compressed to form cores. The cores are compression-coated with a mixture of active ingredient, carbowax 6000, lactose, confectioner's sugar, and talcum.

Starha, L., et al., Chem. Abstracts 75, 40347y (1971) discloses a retarded release tablet containing an active component in admixture with stearic acid or a glycerol mono-, di-, or tri- stearate with the stearic acid or ester being present in concentrations of 5%, 16%, or 25% of the tablet weight. These tablets were not coated.

Bervenmark, H., et al., Acta. Pharm. Suecica 3, 45 (1966). A sustained-release potassium chloride tablet is disclosed in which potassium chloride having a particle size of 10 to 20 microns is distributed homogenously in a fatty base in the proportions of 1:1. Further details as to the composition of this product were not given.

Svedres, E. V., et al., U.S. Pat. No. 2,793,979 patented May 28, 1957, discloses a sustained-release tablet in which a medicament is mixed with a liquified fat or wax which is then caused to solidify and is reduced to a powder, formed into a granulation and compressed into a tablet in admixture with non-sustained release granules of the medicament. The use of fatty acids, fatty alcohols or esters alone or in admixture is disclosed for time-delay purposes.

None of the foregoing references discloses film-coating of a sustained-release fatty matrix core to reduce the initial dissolution rate thereof.

The following references are representative of the tablet film coating art as it is applied to controlled release film coats.

Lehmann, K., Manufacturing Chemist & Aerosol News, May 1973, page 36. General principles of film coating of tablets are reviewed. The article is concerned principally with acrylic films. It is disclosed near the bottom of the first column that the rate of dissolution and the permeability can be adjusted by the proportion of salt-forming and non-ionic hydrophylic and hydrophobic substituent groups of an acrylic resin.

Lehmann, K., ibid., June 1973, page 39. Acrylic film coated tablets are disclosed which are resistent to dissolution in the stomach.

Kassem, et al., Manufacturing Chemist & Aerosol News April, 1973, pages 23–29. Potassium chloride powder is embedded in melted stearic acid and formed into granules which are film coated with sodium alginate, cellulose acetate phthalate and propylene glycol (batch 8, page 25). Small tablets were prepared containing 0.4 g. of potassium chloride per tablet. A high release rate during the first hour compared to the remainder of dissolution period was observed.

Fites, et al., J. Pharm. Sci. 59, pages 610–613, May 1970. The drug permeability properties of several water insoluble films was studied with respect to their potential application for the controlled release of solid pharmaceutical dosage forms. The resins alone and in combination which were studied included cellulose acetate phthalate, ethyl cellulose, hydroxypropyl methyl cellulose, poly(methylvinylether)maleic anhydride, etc. In Table II the water permeability of various polymeric films was reported and an ethyl cellulose-hydroxypropylmethyl cellulose coated tablet released only a small percentage (3%) during 6 hours of dissolution time.

Dow Technical Literature for Methocel ® 60 HG Methylcellulose Product. This undated sales proposal refers to the time release potential of using increasing ratios of ethyl cellulose to hydroxypropyl methyl cellulose in a film coat.

Methocel Product Information, Copyright 1969, Dow Chemical Company. It is indicated in page 1 that Methocel ® adapts easily to time release films.

Film Coating Technology, March 1973, Colorcon, Inc., Moyer Boulevard, West Point, Pa. 19486. Reference is made to the fact that hydroxypropyl methyl cellulose and ethyl cellulose are widely used in film coating, refer to the top of page 2.

SUMMARY OF THE INVENTION

The present invention refers to a pharmaceutical or nutritional tablet which is adapted for continuous release of a water soluble medicament or dietary supplement during a pre-determined dissolution period of at least about 5 hrs., preferably 8 hrs., and up to the transit time for passage through the digestive tract of the mammal being treated. The tablet is intended for use with water soluble medicaments or dietary supplements which are administered in relatively large doses of from about 3 g. to 15 or 20 g. per day. The invention is preferably applicable to controlled release potassium chloride tablets for the prevention and treatment of hypokalemia, but it is also suitable for use with other water soluble drugs and dietary supplements such as oral electrolytes including sodium citrate, sodium phosphate monobasic, sodium chloride, calcium lactate, magnesium sulfate, urinary acidulents such as ammonium chloride and calcium chloride, to water soluble organic compounds such as ascorbic acid, aminoacids, and to potassium iodide, sodium iodide, choline, inositol, potassium phosphate monobasic, and to carbohydrates such as glucose, fructose, and sucrose. When the term "water soluble medicament" is used herein, it is intended to refer to substances having a water solubility of the same order as potassium chloride or greater, or at least about 6 g./100 ml. at 37° C. and which have utility in therapeutics or nutrition when ingested.

The tablet comprises a core constituting about 95% of the tablet weight which is completely enclosed within a permeable erosion resistant polymeric film. The core contains at least 0.75 g., and preferably 0.9 g. or more of the medicament or dietary supplement so that a relatively small number of tablets will be required to administer a relatively large dose. The core is made up of from 72–85% by weight of the water soluble medicament or dietary supplement and from about 13–25% by weight of an insoluble material having a wax-like consistency. The latter forms a matrix from which the water soluble medicament slowly dissolves following ingestion. The preferred wax-like material is stearic acid, but many equivalent materials are known to the art including: beeswax, white wax, carnuba wax, rock wax, vinyl polymers, and combinations of the foregoing, particularly those containing white wax.

The film constitutes up to about 5% of the tablet weight. The film is comprised of a major proportion of a polymeric material or a mixture of polymeric materials and a minor proportion of a plasticiser therefor to lend a relatively elastic or at least non-brittle texture to the film. The film permeability is determined by its thickness, the composition of the polymeric material employed, and the plasticiser. The combination of the components is chosen so that the quantity or weight of the medicament dissolved during the first hour after ingestion or immersion and agitation in water or synthetic gastric fluid is substantially similar to the hourly average amount thereof dissolved during the first three hours of the dissolution period. By substantially similar is meant that the amount of medicament dissolved during the first hour deviates from the average hourly dissolution during the first 3 hours by no more than about 22% of said average. In order to limit the size of the tablet, the film comprises no more than 5% and preferably about 3% by weight of the tablet and thus is a relatively thin film. Sugar coats of the prior art have played no role in controlling the medicament release rate and are of a substantial thickness and weight compared to the tablet as a whole. Selection of the polymeric material and the plasticiser for the film coat are thus important aspects of preparing the present tablet.

BRIEF DESCRIPTION OF THE DRAWING

The drawing constitutes four graphs plotted on the same set of co-ordinates representing the dissolution profile of a tablet constituting the preferred embodiment of the present invention shown by graph I, the dissolution profile of the uncoated core of the same tablet shown by graph II, and the dissolution profile limits for the present invention shown by the two broken lines representing the upper and lower limits.

DESCRIPTION OF SPECIFIC EMBODIMENTS

The controlled release tablet of the present invention provides a solution to a problem encountered in preparing water-insoluble matrix controlled release tablets. The invention is applicable to the design and manufacture of pharmaceutical tablets containing at least 750 mg. and preferably those containing 900 mg. to 1200 mg. of potassium chloride or similar water soluble medicament. The present invention provides a means for limiting the release of medication during the early stages of the dissolution period when there is a tendency for excessive release of medicament to occur. A tablet similar to those of the prior art but containing 750 mg. to 1200 mg. of potassium chloride in the core possess a substantially larger surface area than the prior art tablets and thus in the early stages of dissolution excessive amounts of the active ingredient are released. In order to reduce the amount of dissolution during the early stages of dissolution, it has been found useful to apply a polymeric film coat which is sufficiently durable to remain intact during storage and transport, and sufficiently erosion resistant to remain intact during at least a portion of the dissolution period, but yet which is sufficiently permeable to allow release of the contained medicament at the desired rate.

Three factors are involved in selecting an appropriate film. They are the identity of the polymeric material, the identity of the plasticiser, and the thickness or weight of the film when a uniform continuous film is employed. After preparation of a suitable core, various polymeric materials, plasticisers, and combinations thereof are employed to apply film coats and the dissolution profiles of the resulting coated tablets are compared to those of the uncoated core.

The dissolution profile is the relationship between the amount of medicament dissolved and time period of exposure to the dissolving fluid. It is determined by placing one or more tablets, but preferably one, in a straight walled glass bottle securely closed and containing 50 ml. of water or other liquid test medium which is appropriate for the experiment and rotating the bottle at 2 rpm while immersed in a water bath maintained at constant temperature, preferably 37° C., in such a way that the length of the bottle is parellel to the axis of rotation. A rate of rotation of 2 rpms is employed but higher rates of rotation up to about 40 rpms give substantially the same results. One bottle, but preferably a group of several bottles, is employed for each time period desired in the dissolution profile. Time periods of 1, 3, 5 and 8 hours have been found convenient. One bottle, or group of bottles, is then removed from the constant temperature water bath at each time interval, the tablet residues removed, and the liquid portion saved for analysis for the amount of medicament dissolved during that time period. The procedure is repeated until samples for each test interval have been collected. The various solutions are then analyzed for medicament concentration and a graph is prepared of the cumulative percent dissolved at the various test intervals, This is known as the rolling bottle method.

Various polymeric materials and mixtures thereof which are known to be suitable for tablet film coating may be employed. A film coat which is relatively insoluble in water yet which is erosion resistant and affords the proper medicament dissolution profile is desired. Suitable polymeric materials include cellulose acetate phthalate, shellac, zein, cellulose acetate, hydroxypropyl methylcellulose, hydroxypropyl cellulose, hydrogenated caster oil, ethyl cellulose, poly(methylvinylether)-maleic anhydride, polyvinylacetate phthalate, acrylic resins, stearic acid modified phthalic acid glyceride condensation product, mixtures of the foregoing, and equivalents.

The plasticiser is used in an amount sufficient to afford a durable erosion resistant film, and the identity of the plasticiser plays a role in the dissolution characteristics of the tablet. Accordingly, for a given polymeric material composition, various plasticisers will afford various dissolution rates. Suitable plasticisers include glycerol, diethyl phthalate, propylene glycol, sorbitol, polyethyleneglycol, mono and diglycerides of fatty acids, polyvinylpyrrolidone, and poloxalene (block polymers of ethylene oxide and propylene oxide).

We have found that a mixture of ethyl cellulose, an extremely water insoluble brittle film former, and hydroxypropyl methyl cellulose, a water soluble polymeric material, plasticised with glycerol affords the desired balance between abrasion and erosion resistance and permeability and affords the desired dissolution profile. The preferred combination is 5 parts by weight of hydroxypropyl methylcellulose, 4 parts by weight of ethyl cellulose and 1 part by weight of glycerol. Minor amounts of pigments, colors, etc., may be incorporated into the film coat composition. The preferred film coat weight for a tablet of this invention containing 0.75–1.2 g. of medicament is about 3–4% of the gross weight of the finished tablet, the core constituting the balance of the tablet weight.

The permeability of the film coat is such as to be non-limiting to dissolution of the tablet after the size of the core has been reduced to about one-half its original size through dissolution of the water soluble medicament. The film coat has been found to remain intact during at least a portion of the dissolution period, and preferably for at least about 3 hours. This is evident by inspection of the tablet during the dissolution period when using the rolling bottle test, and also by the fact that the empty coat from which the core has dissolved can sometimes be recovered from the feces.

In some instances it is desirable to apply a decorative finished coat over the delayed released film coat referred to above. The composition of the finish coat is selected so that it will be readily erodible under the dissolution conditions and have no material effect on the rate of dissolution of the medicament from the tablet. Generally speaking, a readily water soluble or water dispersible finish coat is employed and preferably it is of minimal thickness or weight, again for the purpose of achieving the smallest tablet size possible compatible with the large dose of medicament contained therein. For this purpose, water dispersible or water soluble polymeric films are convenient since they may be applied in the same film coating operation as the primary controlled release film coat by simply making appropriate adjustments in the coating solution composition after the primary controlled release coat has been applied. Opacifiers, pigments, colorants, etc. may be included in both the primary controlled release coat and in the decorative finish coat. Selection of ingredients of this type is a matter of choice and is well within the skill of the pharmacist. Suitable water soluble or water dispersible decorative film coat polymers include hydroxypropyl methyl cellulose, polyethylene glycol, polyoxalene, etc.

In preferred embodiments of the present invention which are described in Examples 1 and 2 wherein a primary controlled release film coat comprised of 5 parts by weight of hydroxypropyl methyl cellulose, 4 parts by weight of ethyl cellulose, and 1 part by weight of glycerol is employed, it has been found desirable to apply a decorative finish coat of hydroxypropyl methyl cellulose containing approximately an equal weight of silicon dioxide as opacifier. The finish coat preferably weighs from about 3–10% of the weight of the primary controlled release coat. This decorative finish coat has been found particularly desirable when employing the hydroxypropyl methyl cellulose, ethyl cellulose, and glycerol in the controlled release coat over a stearic acid core tablet because the stearic acid has a tendency to diffuse into the controlled release coat on storage resulting in a mottled or uneven opaque appearance. By employing the hydroxypropyl methyl cellulose silicon dioxide decorative coat, a uniform opaque appearance is conferred upon the tablet.

EXAMPLE 1.

Film Coated Potassium Chloride Controlled Release Tablet Containing 12.5 meq. of Potassium Chloride.- A wet granulation is prepared from the following ingredients.

| Ingredient | Amount |
| --- | --- |
| Potassium Chloride Powder, micropulverized | 937.5 g. |
| Stearic Acid Powder | 187.5 g. |
| Povidone, USP | 10.0 g. |
| Magnesium Stearate | 10.0 g. |
| FD&C Yellow #6, aluminum lake | 1.0 g. |

The povidone (polyvinylpyrrolidone) is dissolved in ten times its weight of water and the solution is added to a dry blend of the potassium chloride powder, stearic acid powder, and FD&C Yellow #6 aluminum lake to form a wet granulation. The latter is dried on trays at a temperature not to exceed 125° F. (52° C.) until the moisture content is 1% or less. It is then comminuted and blended with the magnesium stearate and tableted to give 1,000 tablets having a tablet weight of 1.146 g. and a hardness of 15–21 Strong Cobb Units. The film coat, which is made up of about 40% by weight of ethyl cellulose, about 50% by weight of hydroxypropyl methyl cellulose and about 10% by weight of glycerol, and minor amounts of pigments and dyes, is applied by an air suspension coating process similar to that described in U.S. Pat. No. 3,253,944 of Dale E. Wurster (Wisconsin Alumni Research Foundation, May 31, 1966). The inlet air temperature during the coating process is 110–130° F., preferably 115° F. The pump pressure for the coating solution is 50–80 psig. To provide a low gloss appearance, prolonged tumbling of the coated tablets is avoided and a decorative finish coat of methyl cellulose containing silicon dioxide as opacifier and dyes and weighing 8–9% of the weight of the film coat is applied in a second treatment in the air suspension coating apparatus. Specifically, the film coat solution is comprised of the following ingredients.

| Ingredient | Amount |
| --- | --- |
| Ethyl cellulose | 13.75 g. |
| Methylene Chloride | 355.0 g. |
| Hydroxypropyl Methyl Cellulose | 17.2 g. |
| Alcohol SD#3A | 355.0 g. |
| Glycerol | 3.45 g. |
| Titanium Dioxide | 0.5 g. |
| FD&C Yellow #6, aluminum lake | 0.1 g. |

The decorative finish coat solution is made up of the following ingredients.

| Ingredient | Amount |
| --- | --- |
| Hydroxypropyl Methyl Cellulose | 1.5 g. |
| Methylene Chloride | 50.0 g. |
| Alcohol SD#3A | 50.0 g. |
| Titanium Dioxide | 0.14 g. |
| FD&C Yellow #6, aluminum lake | 0.02 g. |
| Colloidal Silicon Dioxide | 1.5 g. |

Repeated batches of the tablet prepared according to Example 1 are found to have dissolution profiles meeting the following specifications expressed in terms of the percent of potassium chloride contained in the tablet dissolved during the specified time period: 1 hour less than 25%, 3 hours 45–75%, 5 hours at least 66%, 8 hours at least 90%.

Referring to the drawing, Graph I is the dissolution profile of the product of Example 1. The average hourly dissolution during the first three hours is 17.8%. Dissolution during the first hour is 13.7%. The deviation of the latter from the former (4.1%) is 21.6%. Graph II is the dissolution profile of the compressed tablet core of Example 1 prior to applying the film coat.

It is evident that the dissolution profile of the uncoated core falls far outside the specifications required for the preferred tablet of the present invention shown by the broken lines in the drawings. Nearly 60% of the potassium chloride is dissolved from the uncoated core within the first hour with apparently more than 90% dissolution occurring within 3 hours. The hourly average dissolution for the uncoated core during the first three hours is thus about 30%, but the dissolution during the first hour is nearly 60%. The dissolution during the first hour deviates from the average by 100% rather than no more than 22% as required by the present invention.

For the preparation of smaller or larger film-coated potassium chloride controlled release tablets according to the present invention, Example 1 is modified by preparing a tablet core as described modified by scaling the amounts of ingredients on a weight proportional basis to provide the desired quantity of potassium chloride. The amount of film coat ingredients are not adjusted on a weight-proportional basis in this way, however, but rather on the basis of the ratio of the surface areas of the two tablet cores. For example, the following is a description of a preparation of a potassium chloride controlled release tablet according to the present invention containing 10 meq. (750 mg.) of potassium chloride per tablet. This tablet has the same diameter as that of Example 1, but it is thinner.

EXAMPLE 2.

Film Coated Potassium Chloride Controlled Release Tablet Containing 10.0 meq. of Potassium Chloride.— The following ingredients are employed to prepare the tablet core as described in Example 1. The amount of ingredients given is sufficient for 1,000 tablets.

| Tablet Core Ingredients | Amount |
| --- | --- |
| Potassium Chloride, micropulverized | 750.0 g. |
| Stearic Acid Powder | 150.0 g. |
| Povidone, USP | 8.0 g. |
| Magnesium Stearate | 8.0 g. |
| Color, FD&C Blue #2, aluminum lake | 0.5 g. |

The granulation is dried to a moisture content of 0.5% or less, and the tablet cores are compressed to a hardness of 14–16 Strong Cobb Units. Each tablet core weighs 0.9165 g. The film coat and the decorative finish coat are prepared from the ingredients listed below and applied to the tablet core in the same way as is described in Example 1.

| Film Coat Ingredients | Amount |
| --- | --- |
| Ethyl Cellulose | 12.20 g. |
| Methylene Chloride | 310.0 g. |
| Hydroxypropyl Methyl Cellulose | 152.0 g. |
| Alcohol, SD#3A | 310.0 g. |
| Glycerol | 3.00 g. |
| Titanium Dioxide | 0.50 g. |
| Color, FD&C Blue #2 (indigotine) | 0.013 g. |
| Water | 2.7 g. |

| Decorative Finish Coat Ingredients | Amount |
| --- | --- |
| Hydroxypropyl Methyl Cellulose | 1.42 g. |
| Methylene Chloride | 45.0 g. |
| Alcohol, SD#3A | 45.0 g. |

-continued

| Decorative Finish Coat Ingredients | Amount |
|---|---|
| Titanium Dioxide | 0.144 g. |
| Color, FD&C Blue #2 (indigotine) | 0.003 g. |
| Water | 0.7 g. |
| Colloidal Silicon Dioxide | 1.42 g. |

In this instance, the tablet coat constitutes 3.6% by weight of the finished tablet while in Example 1 the tablet coat constituted 3.2% by weight of the finished tablet. The dissolution profile of the tablet core of Example 2 when measured by the rolling bottle method, yielded 36% dissolution of potassium chloride in 15 min., 54% in 30 min., and 71% in 60 min., and 90% dissolution after four hours. The finished tablet bearing the film coat conformed to the same dissolution specifications as the tablet of Example 1.

What is claimed is:

1. A pharmaceutical tablet for continuous release of a medicament during a predetermined dissolution period of at least 5 hrs. and up to 8 hrs. following ingestion by a mammal comprising a core constituting at least 95% of the tablet weight and containing at least 0.75 g. of a water soluble medicament and coated with a permeable erosion resistant polymeric film, said core comprising a compressed granulation containing from 72% to 85% by weight of said core of said water soluble medicament and from 13% to 25% by weight of said core of a water insoluble material having a wax-like consistency said film being continuous and constituting up to 5% of the tablet weight and being comprised of a major proportion of a polymeric material and a minor proportion of a plasticiser therefor wherein said polymeric material, said plasticiser, and the quantities thereof are selected so that said film remains intact for at least a portion of said dissolution period and confers a dissolution profile upon said tablet when measured by the rolling bottle method and expressed as percent by weight of medicament contained in said tablet dissolved per unit of time of from 45 to 75% during the first 3 hours of said dissolution period, a maximum of 25% during the first hour of said dissolution period, at least 66% during the first 5 hours, and at least 90% during the entire 8 hour dissolution period, the amount of medicament dissolved during the first hour of said dissolution period deviating by no more than 22% from the average hourly amount thereof dissolved during the first 3 hours of said dissolution period, and wherein the amount of medicament dissolved during the first hour of said dissolution period from said core in the absence of said film and measured by the rolling bottle method exceeds the average hourly amount thereof dissolved during the first 3 hours of said dissolution period by more than 22%.

2. The tablet of claim 1 wherein said water soluble medicament is potassium chloride.

3. The tablet of claim 1 wherein said water soluble medicament is sodium chloride.

4. The tablet of claim 1 wherein said water insoluble material having a wax-like consistency is stearic acid.

5. The tablet of claim 1 wherein said core constitutes approximately 97% of the tablet weight and said film constitutes approximately 3% of the tablet weight.

6. The tablet of claim 1 wherein said polymeric material is a mixture of hydroxypropyl methyl cellulose and ethyl cellulose.

7. The tablet of claim 1 wherein said polymeric material is a mixture of hydroxypropyl methyl cellulose and ethyl cellulose and said plasticiser is glycerol.

8. The tablet of claim 1 wherein said film contains 9 parts by weight of said polymeric material and 1 part by weight of said plasticiser.

9. The tablet of claim 1 wherein said film contains 5 parts by weight of hydroxypropyl methyl cellulose, 4 parts by weight of ethyl cellulose and 1 part by weight of glycerol.

10. The tablet of claim 1 wherein said film is enclosed within a decorative finish coat, said finish coat being readily erodible from said tablet during said dissolution period.

11. The tablet of claim 1 wherein said core contains at least 0.9 g. of said water soluble medicament.

12. A pharmaceutical tablet for oral potassium treatment by continuous release of potassium chloride during a dissolution period of at least 5 hrs. and up to 8 hrs. following ingestion by a mammal comprising a compressed core coated with a permeable erosion resistant polymeric film, said core containing 937.5 mg. of potassium chloride, 187.5 mg. of stearic acid, and from 20 to 100 mg. of pharmaceutical ingredients selected from the group consisting of lubricants, excipients, binders, and colors, said film being continuous and constituting up to 5% of the tablet weight and being comprised of sufficient of a homogeneous mixture of 5 parts by weight of hydroxypropyl methyl cellulose, 4 parts by weight of ethyl cellulose and 1 part by weight of glycerol to confer a dissolution profile upon said tablet when measured by the rolling bottle method and expressed as percent by weight of potassium chloride contained in said tablet dissolved per unit of time of from 45–75% during the first 3 hours of said dissolution period, a maximum of 25% during the first hour of said dissolution period, at least 66% during the first 5 hrs., and at least 90% during the entire 8-hour dissolution period, the amount of potassium chloride dissolved during the first hour of said dissolution period deviating by no more than 22% from the average hourly amount thereof dissolved during the first 3 hrs. of said dissolution period.

13. The tablet of claim 12 wherein said film is enclosed within a decorative finish coat, said finish coat being erodible from said tablet during said dissolution period at a sufficiently rapid rate as to not materially affect the dissolution profile specified in claim 12.

14. The tablet of claim 12 wherein said decorative coat is comprised of hydroxypropyl methyl cellulose containing opacifiers.

15. The tablet of claim 12 wherein said decorative coat is comprised of about 1.5 mg. of hydroxypropyl methyl cellulose having dispersed therein of an approximately equal weight of silicon dioxide.

16. A pharmaceutical tablet for oral potassium treatment by continuous release of potassium chloride during a dissolution period of at least 5 hrs. and up to 8 hrs. following ingestion by a mammal comprising a compressed core coated with a permeable erosion resistant polymeric film, said core containing 750 mg. of potassium chloride, 150 mg. of stearic acid, and from 16 to 80 mg. of pharmaceutical ingredients selected from the group consisting of lubricants, excipients, binders, and colors, said film being continuous and constituting about 3.6% of the tablet weight and being comprised of a homogeneous mixture of 5 parts by weight of hydroxypropyl methyl cellulose, 4 parts by weight of ethyl cellulose and 1 part by weight of glycerol wherein the dissolution profile of said tablet when measured by the rolling bottle method and expressed as percent by weight of potassium chloride contained in said tablet dissolved per unit of time is from 45-75% during the first 3 hours of said dissolution period, a maximum of 25% during the first hour of said dissolution period, at least 66% during the first 5 hrs. of said dissolution period, and at least 90% during the entire 8-hour dissolution period, the amount of potassium chloride dissolved during the first hour of said dissolution period deviating by no more than 22% from the average hourly amount thereof dissolved during the first 3 hrs. of said dissolution period.

17. The tablet of claim 16 wherein said film is enclosed within a decorative finish coat, said finish coat being erodible from said tablet during said dissolution period at a sufficiently rapid rate as to not materially affect the dissolution profile specified in claim 16.

18. The tablet of claim 16 wherein said decorative coat is comprised of hydroxypropyl methyl cellulose containing opacifiers.

19. The tablet of claim 16 wherein said decorative coat is comprised of about 1.4 mg. of hydroxypropyl methyl cellulose having dispersed therein of an approximately equal weight of silicon dioxide.

* * * * *